(12) United States Patent
Kawaguchi et al.

(10) Patent No.: US 9,934,946 B2
(45) Date of Patent: Apr. 3, 2018

(54) PLASMA PROCESSING APPARATUS AND OPERATING METHOD OF PLASMA PROCESSING APPARATUS

(71) Applicant: Hitachi High-Technologies Corporation, Tokyo (JP)

(72) Inventors: Yohei Kawaguchi, Tokyo (JP); Tatehito Usui, Tokyo (JP); Masahito Togami, Tokyo (JP); Satomi Inoue, Tokyo (JP); Shigeru Nakamoto, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/277,272

(22) Filed: Sep. 27, 2016

(65) Prior Publication Data
US 2017/0178874 A1 Jun. 22, 2017

(30) Foreign Application Priority Data
Dec. 17, 2015 (JP) .................. 2015-245786

(51) Int. Cl.
*G01B 11/06* (2006.01)
*H01L 21/3065* (2006.01)
(Continued)

(52) U.S. Cl.
CPC .... *H01J 37/32972* (2013.01); *G01B 11/0616* (2013.01); *G01N 21/84* (2013.01);
(Continued)

(58) Field of Classification Search
None
See application file for complete search history.

(56) References Cited

U.S. PATENT DOCUMENTS

2003/0043383 A1* 3/2003 Usui .................. G01B 11/0675
356/504
2004/0192056 A1* 9/2004 Iijima ............... H01L 21/32137
438/706
(Continued)

FOREIGN PATENT DOCUMENTS

JP 2011-528967 A 12/2011
JP 2014-072264 A 4/2014
(Continued)

OTHER PUBLICATIONS

Korean Office Action received in corresponding Korean Application No. 10-2016-0122799 dated Jul. 13, 2017.
(Continued)

*Primary Examiner* — Shamim Ahmed
(74) *Attorney, Agent, or Firm* — Mattingly & Malur, PC

(57) ABSTRACT

A plasma processing device performing etching processing to a sample disposed in a processing chamber disposed in a vacuum vessel by using plasma formed in the processing chamber includes a light detector, a component detector, and a determination unit. The light detector detects light intensity of a plurality of wavelengths from the inside of the processing chamber at a plurality of times during the sample processing. The component detector detects, by using a result of a principal component analysis of time-series data, a highly correlated component between the time-series data of a plurality of the wavelengths at a certain time in a plurality of the times obtained from output of the light detector. The determination unit determines an amount or an end point of the etching processing based on a change in light intensity of at least one of a plurality of the wavelengths detected by using the time-series data from which the highly correlated component is removed.

5 Claims, 6 Drawing Sheets

(51) Int. Cl.
*H01L 21/66* (2006.01)
*G01N 21/84* (2006.01)
*H01J 37/32* (2006.01)

(52) U.S. Cl.
CPC .. *H01J 37/32935* (2013.01); *H01J 37/32963* (2013.01); *H01L 21/3065* (2013.01); *H01L 22/26* (2013.01); *H01J 37/32715* (2013.01); *H01J 37/32834* (2013.01); *H01J 2237/334* (2013.01)

(56) References Cited

U.S. PATENT DOCUMENTS

2008/0216956 A1* 9/2008 Nakamoto ......... G01B 11/0625
　　　　　　　　　　　　　　　　　　　　　　　　156/345.25
2014/0295583 A1* 10/2014 Nakamoto ............. H01L 22/12
　　　　　　　　　　　　　　　　　　　　　　　　438/16

FOREIGN PATENT DOCUMENTS

| KR | 10-2014-0118666 A | 10/2014 |
| TW | 201435621 A | 9/2014 |

OTHER PUBLICATIONS

Taiwanese Office Action received in corresponding Taiwanese Application No. 105131351 dated Apr. 27, 2017.

* cited by examiner

PLASMA PROCESSING APPARATUS AND OPERATING METHOD OF PLASMA PROCESSING APPARATUS

BACKGROUND OF THE INVENTION

The present invention relates to a plasma processing device and an operation method for the plasma processing device. The plasma processing device and the operation method are a plasma processing device and a plasma processing method in which a process to manufacture a semiconductor integrated circuit is used, and a substrate-like sample such as a semiconductor wafer disposed in a processing chamber in a vacuum vessel is processed by using plasma formed in the processing chamber. The plasma processing device and the operation method detect a film thickness or a processing amount of a sample surface by using light emission from the inside of the processing chamber detected during the processing.

A process to manufacture a semiconductor device includes processing to form a circuit pattern of a semiconductor device, so-called dry-etching processing, by etching a film structure including a plurality of film layers including a dielectric material and a mask layer formed on a sample surface by disposing a substrate-like sample of such as a semiconductor wafer in a processing chamber in a vacuum vessel and using plasma formed in the processing chamber. In such etching processing, it is desired to further accurately determine an etching end point and appropriately control processing conditions to realize a recently increasing integration degree of a semiconductor device and to realize a highly accurate circuit pattern by stopping the processing at a desirable film thickness or a desired etching depth of the above-described film layer.

In general, in such etching processing, in a state in which a semiconductor wafer is disposed in a processing chamber in a vacuum vessel, an electric field or a magnetic field is supplied to processing gas supplied in the processing chamber, and plasma is formed by exciting atoms or molecules of the gas. The processing on a film structure on a sample is performed by using the plasma. During the processing, light intensity of a specific wavelength included in light emission of the plasma in the processing chamber is changed in association with an etching progress of a specific film to be processed or a certain film on which the processing is progressing.

Therefore, conventionally, as a technique to accurately detect an end point of the processing, a technique is known which detects a change in intensity of the specific wavelength included in a light emission from a processing chamber during etching processing and detects an end point of the processing based on a result of the above detection. However, the above-described light emission generally includes light emission of relatively less correlated wavelengths other than light emission of a specific wavelength generated by reaction significantly correlated to the processing. When the end point is determined, it is necessary to reduce and suppress miss-detection due to a change in a waveform of a wavelength to be detected, which is caused by such noise.

JP-2014-72264-A describes a technique to accurately detect a change in the intensity of light emission in association with the noise. This conventional technique uses a plasma processing device which performs etching processing on a sample disposed in a processing chamber disposed in a vacuum vessel by using plasma formed in the processing chamber. JP-2014-72264-A discloses a plasma processing device to determine an etching processing amount based on a result in which in-phase components changed by time in an increase or decrease direction together by synchronizing between light emission intensity of a plurality of wavelengths are removed from data of the light emission intensity detected from output from a light receiver which receives light emission from the inside of the processing chamber. Especially, in an example described herein, time-series data indicating the intensity of light emission of a plurality of wavelengths obtained from a spectroscope is sent to an in-phase component removing device to remove the in-phase components. Then, after average components are removed from a difference in data for each time, a characteristic vector is calculated which includes a base corresponding to the in-phase components by performing a principal component analysis about a matrix including data of each wavelength as an element.

Further, a base vector calculated from the characteristic vector is sent to a Kalman filter, in-phase components are removed from a difference in each of the above-described wavelengths by the Kalman filter, and the difference from which the in-phase components are removed is integrated and restored as a time waveform for each wavelength. In the conventional technique, time-series data is used which is restored by removing noise component described above and which indicates light emission intensity, and a technique to highly accurately detect an etching amount or an etching end point is indicated.

SUMMARY OF THE INVENTION

The above-described conventional technique has a problem since the following points are insufficiently considered.

Specifically, although the technique disclosed in JP-2014-72264-A effectively removes noise component including in-phase components suddenly generated between light emission of a plurality of wavelengths from a signal of each wavelength, when a ratio of the in-phase components in a change by time in data obtained from the light emission is increased, the in-phase components do not follow the change and are left, and artifacts (virtual image) are generated which have a skirt left for a long time with high intensity. It is known that the intensity of such artifacts is increased as in-phase components are increased, and the skirt is left for a longer time. When such artifacts are generated, an end point indicated as a change in relatively small light emission intensity is buried into a change by the artifacts and is not highly accurately determined.

Further, removal of in-phase components by the Kalman filter in the conventional technique is non-linear processing. Therefore, since a waveform indicated by time-series data of original light emission intensity is distorted, a change in the intensity corresponding to the above-described end point is buried into this distortion, and the end point cannot be determined at a high accuracy.

An object of the present invention is to provide a plasma processing device and an operation method for the plasma processing device, which can highly accurately detect a residual film thickness and an etching amount.

The above-described object is achieved by a plasma processing device performing etching processing to a sample disposed in a processing chamber disposed in a vacuum vessel by using plasma formed in the processing chamber. The plasma processing device includes a light detector, a component detector, and a determination unit. The light detector detects light intensity of a plurality of wavelengths from the inside of the processing chamber at a plurality of times during the sample processing. The component detector detects, by using a result of a principal component analysis of time-series data, a highly correlated component between the time-series data of a plurality of the wavelengths at a certain time in a plurality of the times obtained from output of the light detector. The determination unit determines an amount or an end point of the etching processing based on a change in light intensity of at least one of a plurality of the wavelengths detected by using the time-series data from which the highly correlated component is removed.

According to the present invention, especially in an etching processing device in the plasma processing device, even if a change in a desired light emission intensity is relatively minute with respect to in-phase components included in a light intensity signal obtained from a processing chamber during a plasma-used processing, a change in the intensity can be highly accurately detected by generating a waveform of a signal in which the in-phase components are reduced. Based on data of the signal generated in this manner, an actual etching amount and end point of a processed layer can be further accurately detected.

DESCRIPTION OF THE EMBODIMENTS

An embodiment of the present invention will be described below with reference to the drawings.

In the embodiment of the present invention, a plasma processing device and an operation method for the plasma processing device will be described. The plasma processing device detects an etching amount and determines an etching end point by using light emission from the inside of a processing chamber which includes light reflected by a film structure of a sample surface when etching the film structure including a plurality of layers by using plasma formed in the processing chamber. The layers include a mask layer and a film layer to be processed disposed in advance on an upper surface of the substrate-like sample such as a semiconductor wafer disposed in the processing chamber in a vacuum vessel. Especially, according to the example, the plasma processing device and the operation method for the plasma processing device are disclosed. The plasma processing device and the operation method can effectively remove noise component generated in-phase to time-series data indicating the intensity of interference light having a plurality of wavelengths formed by light reflected by a plurality of film layers on a sample surface, highly accurately detect an etching amount or an etching end point on the film layer to be processed in the film structure, and approach to an original pattern shape forming a circuit of a semiconductor device formed by etching the film structure.

Figure 5:
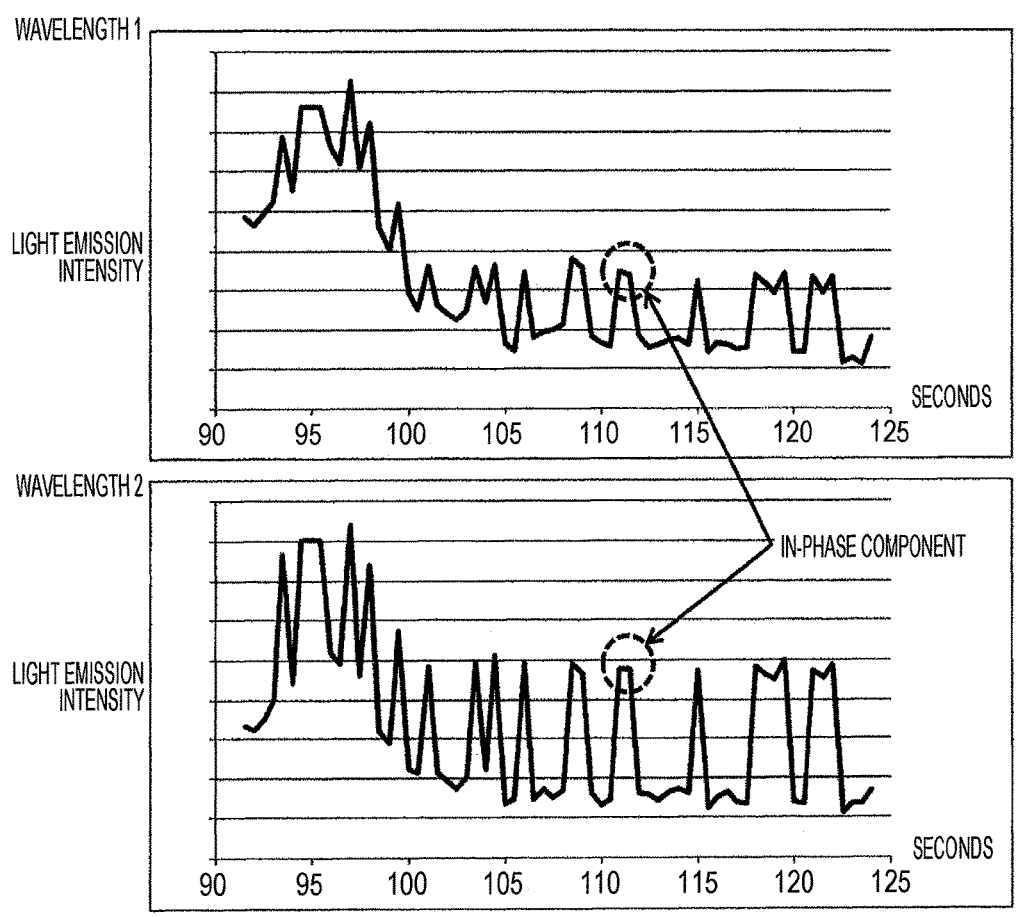
FIG. 5 is a graph illustrating an example of a change in association with a time change in the intensity of light emission of a plurality of wavelengths detected by receiving the light emission from the inside of a processing chamber, according to an embodiment described herein or a conventional technique.

FIG. 5 illustrates an example of a change (hereinafter called a time waveform) in association with a time change of a signal indicating the detected intensity of light emission from the inside of a processing chamber. FIG. 5 is a graph illustrating an example of a change in association with a time change in the intensity of light emission of a plurality of wavelengths detected by receiving the light emission from the inside of a processing chamber, according to the embodiment or a conventional technique.

In FIG. 5, broken lines indicate timings when the intensity of wavelengths is increased (by synchronizing) at each of a plurality of wavelengths simultaneously or at an approximate time regarded as simultaneous. These are a sudden change generated in a significantly short time to indicate whether each of the wavelengths included in light emission from a processing chamber is not correlated to other times. Hereinafter, such change and fluctuation are called "in-phase" change and fluctuation.

When a frequency analysis is performed to the time waveform indicating light emission intensity regarding a time direction, the "in-phase" component included in the time waveform of each wavelength is detected as a sudden impulse signal. An object of the embodiment is to realize the plasma processing device and the operation method for the plasma processing device which highly accurately detect an etching amount or an etching end point by removing the sudden impulse signal from the time waveform at high speed and a high accuracy.

Figure 6:
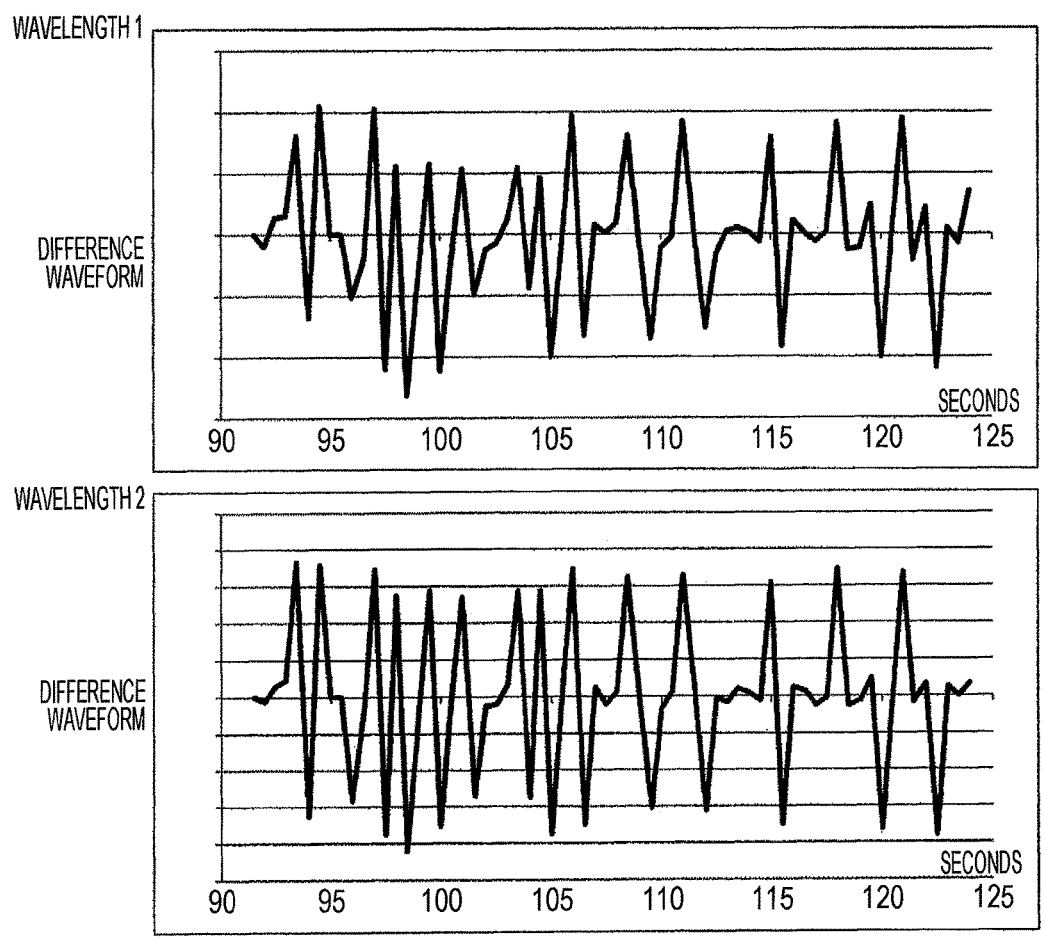
FIG. 6 is a graph illustrating a time difference at each time in the change in association with the time change in the intensity of light emission of a plurality of the wavelengths illustrated in FIG. 5.

Regarding the time-series data of light emission intensity of a plurality of the wavelengths illustrated in FIG. 5, FIG. 6 illustrates a waveform in which a time difference is detected at each time in data of each wavelength. FIG. 6 is a graph illustrating a time difference at each time in the change in association with the time change in the intensity of light emission of a plurality of the wavelengths illustrated in FIG. 5.

As illustrated in the drawing, data indicating the intensity of light emission of different wavelengths from a processing chamber is highly correlated to each time in a time difference value of the time waveform. According to the embodiment, an in-phase component is removed by using the above-described property.

First Example

An example of the present invention will be described with reference to FIGS. 1 to 4.

Figure 1:
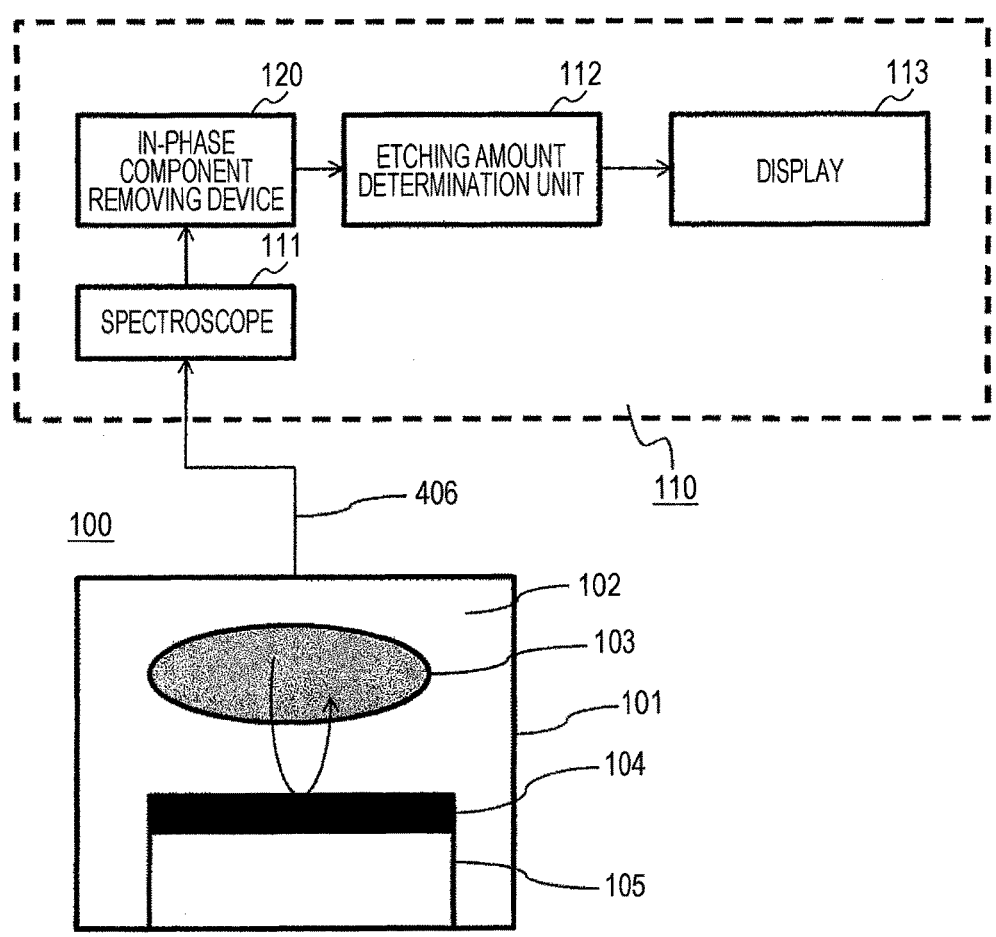
FIG. 1 is a diagram schematically illustrating an outline of a configuration of a plasma processing device according to an example of the present invention.

A configuration of the plasma processing device according to the example will be described with reference to FIG. 1. FIG. 1 is a diagram schematically illustrating an outline of a configuration of a plasma processing device according to the example of the present invention. Especially, a plasma processing device 100 according to the example is a device used in a process to manufacture a semiconductor device by performing an etching processing on a substrate-like sample such as a semiconductor wafer carried in a processing chamber disposed therein. The plasma processing device 100 is a plasma etching device including a detector for detecting an etching amount of the treated sample, for example, a residual film thickness of a mask and a film layer to be processed and the depth of a groove or a hole formed by etching and controlling processing of a sample such as a semiconductor wafer based on output from the detector.

The plasma processing device 100 according to the example includes a vacuum vessel 101, a plasma forming device, and an exhaust device. The vacuum vessel 101 has a cylindrical appearance in which a processing chamber 102 having a cylindrical shape inside is disposed. The plasma forming device is a means to form an electric field and a magnetic field supplied to form a plasma 103 in a space in the processing chamber 102 disposed to the outside of the vacuum vessel 101. The exhaust device is connected to the plasma forming device at a bottom of the vacuum vessel 101 and includes a vacuum pump such as a turbo molecule pump that exhausts ions, highly active particles, and the like forming atoms and molecules of gas and the plasma 103 from the space in the processing chamber 102 and a controller to control a flow amount or a speed of the exhaust air.

In addition, a sample stand 105 is disposed on a lower side of the space in the processing chamber 102, in which the plasma 103 is formed. The sample stand 105 has a round upper surface, and a substrate-like sample 104 such as a semiconductor wafer to be processed is placed on the upper surface. Further, although it is not illustrated, in the example, a gas introducing hole to introduce processing gas to process the sample 104 by forming the plasma 103 is disposed on an inner side of the processing chamber 102, and also the vacuum vessel 101 is connected to a gas pipeline forming a gas supply passage. The gas supply passage connects between the gas introducing hole and a gas source of the processing gas and includes a flow controller to appropriately control a gas flow amount and a gas flow speed in a middle of the passage.

Furthermore, the plasma processing device 100 according to the example includes an etching amount detector 110. The etching amount detector 110 is disposed on the outside of the vacuum vessel 101, receives light emission of the plasma 103 generated during processing of the sample 104 performed in the processing chamber 102 by using the plasma 103 and light from an inner side of the processing chamber 102 such as interference light from a surface of the sample 104, detects a change and intensity of the light, and detects a residual film thickness and an etching amount (for example, the depth of a groove and a hole) of a film layer and to be etched disposed on a surface of the sample 104. In addition, to transmit the light from the processing chamber 102 during the processing to the etching amount detector 110, a window member formed of a translucent material such as quarts is disposed by airtightly sealing the inside and the outside by a sealing member such as an O ring in a through hole disposed to a member forming a side wall of the vacuum vessel 101 surrounding the processing chamber 102 and a cover of the vacuum vessel 101 on an upper side of the processing chamber 102.

In the plasma processing device 100, a side wall of the vacuum vessel 101 is connected to a vacuum conveying vessel. The vacuum conveying vessel is another vacuum vessel (not illustrated) and includes a vacuum conveying chamber which is a decompressed space and conveyed by being held on an arm of a robot in which the sample 104 to be processed is disposed inside. The sample 104 which is not processed is held on an arm of the robot and conveyed in the vacuum conveying chamber, and by extension of the arm, the sample 104 on the arm is conveyed in the processing chamber 102 through the inner side of a passage communicating between the vacuum conveying chamber and the processing chamber 102.

The sample 104 conveyed in the processing chamber 102 is delivered to the sample stand 105 and placed on a round upper surface of a dielectric film covering an upper portion of the sample stand 105. When an opening on a side of the vacuum conveying chamber on the passage through which the sample 104 has passed is closed by a gate valve (not illustrated), and the inside of the processing chamber 102 is airtightly sealed, the sample 104 is held on the dielectric film by an electrostatic force generated by a DC power supplied to an electrode in the dielectric film. Then, processing gas from a gas source is supplied in the processing chamber 102 from a gas introducing hole by appropriately controlling a flow amount and a flow speed by a flow controller, and the gas in the processing chamber 102 is discharged to the outside by operating a vacuum pump included in an exhaust device through an exhaust opening disposed on a lower side of the sample stand 105 and disposed to face the processing chamber 102.

A pressure on an inner side of the processing chamber 102 is controlled to a value within a range appropriate to processing of the sample 104 by balance between a flow amount or a flow speed of processing gas supplied to the processing chamber 102 and a flow amount or a flow speed of air exhausted from an exhaust opening by operating a vacuum pump. The plasma 103 is formed in an upper space of the sample 104 held on the sample stand 105 or an upper surface of the sample stand 105 in the processing chamber 102 by supplying an electric field or a magnetic field formed by a plasma forming device in the processing chamber 102 and by exciting atoms or molecules of processing gas.

A metal disk or a cylindrical electrode (not illustrated) is disposed in the sample stand 105 and electrically connected to a high frequency power source (not illustrated) disposed on the outside of the vacuum vessel 101. In a state in which the plasma 103 is formed, a high frequency power having a frequency different from an electric field of the plasma forming device is supplied to an electrode disposed in the sample stand 105 from the high frequency power source, and a bias potential in response to a potential of the plasma 103 is formed in the processing chamber 102 on an upper side of an upper surface of the sample 104.

Charged particles such as ions in the plasma 103 are excited on an upper side of an upper surface of the sample 104 according to a potential difference between the bias potential and a potential of plasma and collide with a surface of a film structure including a plurality of film layers including mask layers formed of an organic material disposed in advance on the upper surface of the sample 104 and film layers to be processes. In this manner, etching processing on film layers on a surface of the sample 104 is proceeded, physical or chemical reaction is accelerated between highly reactive active atoms or molecules, such as radical in the plasma 103 and a surface of a film layer to be processed. Accordingly, during processing of a film layer to be processed in which an anisotropic processing is accelerated regarding a direction in which charged particles of the film layer to be processed is excited, light is emitted due to active species in the plasma 103 and reaction products generated by an interaction between the plasma 103 having the physical or chemical reaction and a surface of the sample 104.

According to the example, light emission generated in the processing chamber 102 during the processing is detected during the processing by the etching amount detector 110, a processing amount (for example, the residual film thickness of a mask layer such as photoresist disposed on a film to be processed or an upper side of the film, and the etching depth of a groove and a hole formed on the film to be processed) is highly accurately detected, and determination of end point of the processing, a flow amount of processing gas to be supplied, a pressure in the processing chamber 102, values of intensity of an electric field or a magnetic field to form plasma, and conditions on processing such as distribution of the values can be controlled. The etching amount detector 110 includes a light receiver and a spectroscope 111. The light receiver is disposed on an outer side of a window member and receives light from the inside of the processing chamber 102 passing through the window member. The spectroscope 111 decomposes light transmitted from the light receiver via a transmitter such as an optical fiber 106 into a plurality of spectra each having a predetermined frequency or wavelength. Especially, according to the example, a light source for measurement (not illustrated) (for example, a halogen light source) is included in the spectroscope 111. Multiwavelength light emitted from the light source is introduced to a film structure on a surface of the sample 104 disposed on an upper surface of the sample stand 105 in the processing chamber 102 through a window member via the optical fiber 106.

In the example, the window member is disposed in a through hole formed on a member forming a ceiling surface of the processing chamber 102 disposed to face an upper surface of the sample 104 on an upper side of the processing chamber 102 and disposed to face the plasma 103. The light emitted from the light source for measurement enters the processing chamber 102 through the window member at an angle vertical to an upper surface of the sample 104 or an approximate angle regarded as vertical. The emitted light that reaches the upper surface of the sample 104 is reflected toward the processing chamber 102 on a boundary surface between a plurality of film layers of a film structure disposed in advance on the upper surface of the sample 104 and transmitted to a light receiver of the etching amount detector 110 and the spectroscope 111 optically or electrically connected to the light receiver via the optical fiber 106 through the window member again.

The emitted light that vertically enters a surface of the sample 104 and is reflected on a plurality of boundaries between a plurality of the film layers having different film structures and disposed at positions in a depth direction becomes interference light mutually interfering and having intensity according to a distance between the depth positions. The intensity of light of each wavelength of such interference light by emitted light including a plurality of wavelengths is introduced in the spectroscope 111 and detected by being decomposed for each wavelength.

The etching amount detector 110 according to the example has functions to reduce in-phase components to be described later from a signal of the intensity of interference light detected during processing of the sample 104 and can highly accurately detect a film layer to be processed on the sample 104, for example, an etching depth and a residual film thickness of a polysilicon film or a residual film thickness of a mask layer. Further, the etching amount detector 110 can highly accurately determine whether to reach an end point in the etching processing.

Signals indicating the intensity of interference light of a plurality of predetermined wavelengths detected by the spectroscope 111 are sent to the in-phase component removing device 120 electrically connected to the spectroscope 111. Then, components included in time waveforms of light having a plurality of wavelengths from the inside of the processing chamber 102 indicated by the signals and changed in phase between the signals of the intensity of light having a plurality of wavelengths are removed. In the in-phase component removing device 120, signals of the time waveforms indicating the intensity of light of a plurality of wavelengths from which in-phase components are removed are sent to the etching amount determination unit 112.

In the etching amount determination unit 112, an etching amount is detected and an end point is determined from waveform signals after noise is removed from received signals. As a technique to determine the etching amount or the end point, for example, the conventional publicly known technique described in JP-2007-234666-A can be used. In addition, in the example, the etching amount of the sample 104 detected by the etching amount determination unit 112 is displayed by being sent to a display 113 including such as a CRT monitor and a liquid crystal monitor.

As described above, time waveforms of the signals indicating the intensity of light having a plurality of wavelengths of the interference light output from the spectroscope 111 is sent to the in-phase component removing device 120. In-phase components included in the sent signals are removed from the signals indicating a time waveform of each wavelength in the in-phase component removing device 120 every time when a waveform of the signal is obtained at a sampling time at predetermined intervals or after waveforms of light emission signals detected in a whole period in which film layers to be processed in a film structure on a surface of the sample 104 are processed are obtained. As a result, a time waveform of each wavelength in which negative influence on the above determination is reduced can be obtained.

Figure 2:
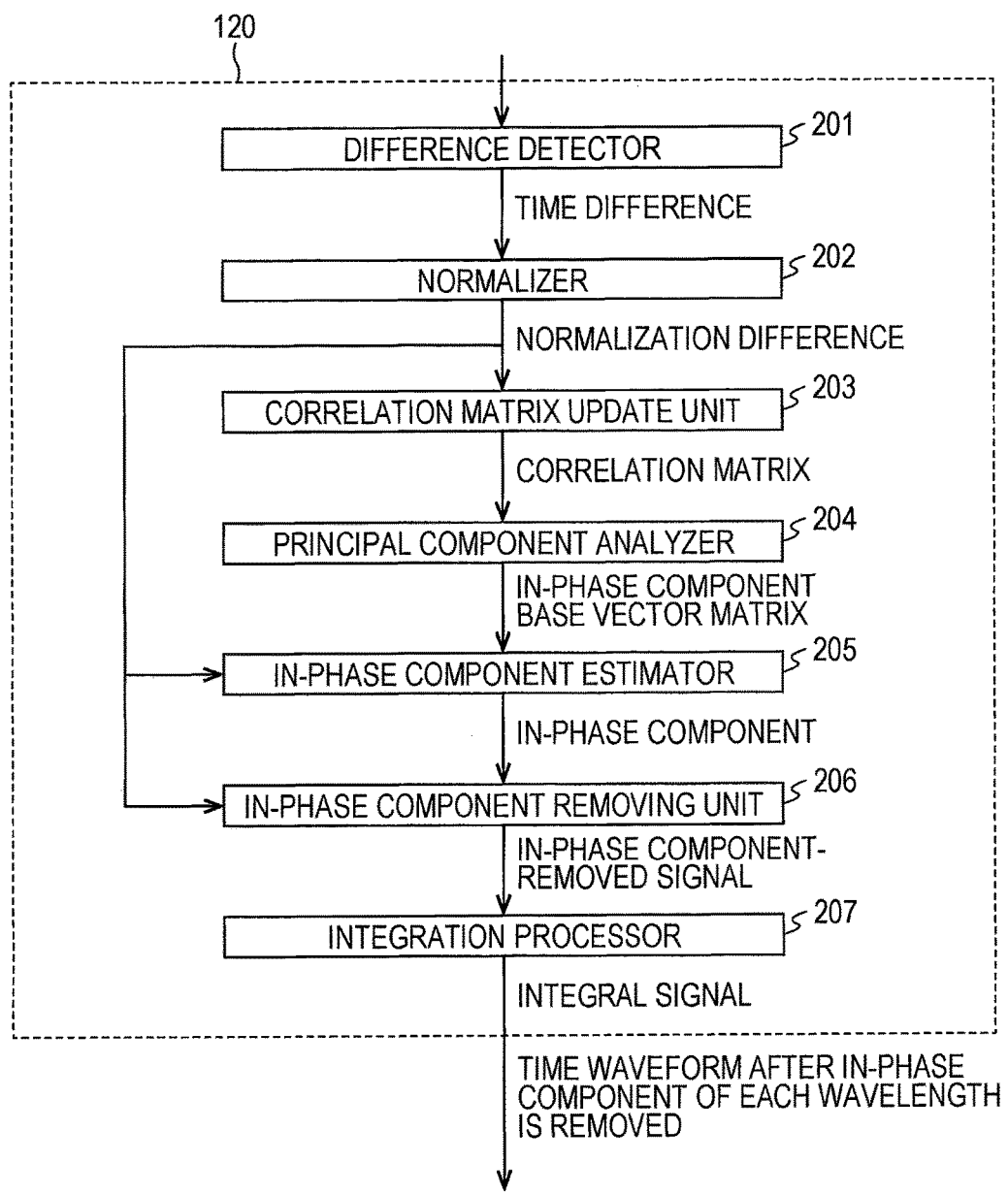
FIG. 2 is a block diagram schematically illustrating a configuration of an in-phase component removing device included in an etching amount detector illustrated in FIG. 1.

Next, a configuration of the in-phase component removing device 120 according to the example will be described with reference to FIG. 2. FIG. 2 is a block diagram schematically illustrating a configuration of an in-phase component removing device 120 included in an etching amount detector 110 illustrated in FIG. 1.

In FIG. 2, signals indicating the intensity of interference light for each of the wavelengths output from the spectroscope 111 and sent to the in-phase component removing device 120 are first sent to a difference calculation unit 201, and a time difference of a time waveform for each wavelength is calculated. By using the time difference, a time waveform being less affected by long-term trend components included in a time waveform of each wavelength is obtained.

A signal indicating a time difference of the intensity of interference light for each wavelength detected by a difference calculation unit 201 is sent to a normalizer 202, and time average values of these time difference signals, and time standard deviation values, and values (normalization difference signals) obtained by subtracting the time average values from the time difference signals and dividing the resultant value by the time standard deviation values are calculated. Consequently, it is expected to further reduce long-term influence by trend components, and also an influence by an intensity difference for each wavelength can be reduced.

Next, the normalization difference signal calculated by the normalizer 202 is sent to a correlation matrix update unit 203. The correlation matrix update unit 203 updates a correlation matrix based on the received normalization difference signal.

A signal indicating the correlation matrix calculated and updated by the correlation matrix update unit 203 is sent to a principal component analyzer 204. The principal component analyzer 204 performs a principal component analysis to a correlation matrix indicated by the received signal and calculates a base vector, which forms an orthonormal base corresponding to a correlation matrix, and a characteristic value of each base vector. Further, the principal component analyzer 204 generates an in-phase component base vector matrix including the base vectors corresponding to an in-phase component.

The in-phase component base vector matrix calculated by the principal component analyzer 204 is sent to the in-phase component estimator 205 as a signal. The in-phase component estimator 205 estimates in-phase components based on a signal indicating a base vector sent from the principal component analyzer 204 and the received normalization difference signal sent from the normalizer 202. The in-phase component estimator 205 according to the example estimates in-phase components by using verification whether in-phase component intensity is a random variable in accordance with an assumed distribution. As a result, even in the case where a change in the intensity of interference light is not orthogonal to an in-phase component, the in-phase component can be effectively removed while suppressing that a change in the intensity of interference light is removed from data indicated by the signal.

A signal of the data indicating in-phase components estimated by the in-phase component estimator 205 is sent to the in-phase component removing unit 206. The in-phase component removing unit 206 removes an in-phase component indicated by a received signal sent from the in-phase component estimator 205 from a received signal indicating the normalization difference sent from the normalizer 202 and calculates in-phase component-removed signal.

The in-phase component-removed signal generated by the in-phase component removing unit 206 is sent to an integration processor 307. The integration processor 307 integrates the received in-phase component-removed signal for each wavelength by a time and restores a time waveform of each wavelength. A time waveform signal indicating a change in the intensity of interference light of the restored wavelengths is sent to the etching amount determination unit 112, and an etching amount of the sample 104 is calculated.

Next, details of processing performed in each block indicated in FIG. 2 will be described.

First, in the example, for convenience, a time waveform signal indicating a change in light intensity of each wavelength from the processing chamber 102 output from the spectroscope 111 at a certain time t in a predetermined period during processing of the sample 104 is indicated by $y\_n, t$ for each wavelength. "n" is an index indicating a wavelength. In the example, "n" may be an index regularly increasing and decreasing from a short wavelength to a long wavelength or may be an index reassigned by picking up a plurality of appropriately selected wavelengths. "t" is a time index.

The difference calculation unit 201 calculates a difference value $\Delta y\_n, t$ for each wavelength from $y\_n, t$. As an example in a calculation procedure, the difference value may be calculated by $\Delta y\_n, t = y\_n, t - y\_\{n, t-1\}$. Here, $\Delta y\_n, t=0$ is established at an initial sample point.

The difference may be substituted by inclination of a first regression coefficient and may be substituted by inclination of a second difference and a second regression coefficient. In addition, in the case where a signal for each time is obtained for each unit time, a difference calculation can be performed for each sample.

In the case where samples of all the time are obtained at one time (off-line processing), difference values of all the time may be calculated by batch processing. As described above, in all of the processing in the present invention, in the case where data is obtained for each sample, processing is performed for each sample, and in the case where samples are obtained at one time, processing is performed at one time.

In the normalizer 202, a time average value $\mu\_n, t$ of a difference value for each wavelength $\Delta y\_n, t$ may be calculated, for example, by a moving average formula. Further, in off-line processing, the time average value may be calculated by an ensemble average formula. Furthermore, a time standard deviation $\sigma\_n, t$ is calculated, for example, as a square root of a movement average of $(\Delta y\_n, t-\mu\_n, t)^2$.

In the off-line processing, the time average value may be calculated by the ensemble average formula. Further, a normalization difference signal is calculated as $z\_n, t=(\Delta y\_n, t-\mu\_n, t)/\sigma\_n, t$.

In the correlation matrix update unit 203, a correlation matrix is updated based on the normalization difference signal $z\_n, t$. Here, in the example, $z\_t=[z\_1, t \ldots z\_N, t]^T$ is defined as a vector having, as an element, each wavelength value $z\_n, t$ of the normalization difference signal sent from the normalizer 202. However, "T" is an operator indicating a transport, and "N" is a number of a wavelength.

The correlation matrix update unit 203 calculates a product of the vector $z\_t$ indicating a normalization difference signal of light intensity of a plurality of wavelengths and a transport vector $z\_t^T$ of the normalization difference signal, and calculates a matrix of N rows and N columns $r\_t$. Further, a correlation matrix $R\_t$ for each time is calculated from $r\_t$, for example, by $R\_t=\alpha(R\_\{t-1\})+(1-\alpha)R\_t$. Here, "$\alpha$" is a moving average coefficient and set to a value of 0 or more and 1 or less such as 0.99 and 0.9.

The principal component analyzer 204 performs a principal component analysis to the correlation matrix $R\_t$ indicated by a received signal sent from the correlation matrix update unit 203 and calculates a base vector $f\_k$ ($k=1, \ldots, N$) forming an orthonormal base corresponding to the correlation matrix $R\_t$ and a characteristic value $\lambda\_k$ of each base vector.

To effectively detect an in-phase component by the in-phase component removing device 120, it is necessary to appropriately select the base vector $f\_k$ corresponding to the in-phase component from a base obtained as a result of operation of the principal component analyzer 204. Since an in-phase component is generated by synchronizing between time waveform data of a plurality of wavelengths, inventors of the present invention have considered that a base vector of an in-phase component is highly correlated to a direction vector of the in-phase such as $[1, 1, \ldots 1]$ and $[-1, -1, \ldots -1]$.

Therefore, in the case of $b=[1, 1, \ldots 1]$, a value obtained by multiplying an absolute value of an inner product of b and $f\_k$ by a characteristic value is indicated by $c\_k=\lambda\_k|b^T f\_k|$. $|b^T f\_k|$ is a value from 0 to 1. However, in the case where $f\_k$ is in-phase, $|b^T f\_k|$ may be a large value close to 1.

In addition, it is thought that an in-phase component needs to be suppressed as the intensity thereof is increased. However, the intensity level is indicated by the characteristic value $\lambda\_k$, and therefore, it is thought that $c\_k$ obtained by multiplying the characteristic value $\lambda\_k$ is appropriate to select an in-phase component to be suppressed. Therefore, according to the example, an in-phase component base vector matrix P is calculated which has r row vectors having large $c\_k$ in the base vectors.

The in-phase component estimator 205 calculates a column vector of an r row $a\_t=P \times z\_t$ by multiplying the received in-phase component base vector matrix P sent from the principal component analyzer 204 and a signal z_t indicating a vector of a received normalization difference sent from the normalizer 202 a_k, t which is kth element of a_t indicates the intensity of kth in-phase base vector included in z_t.

In the case where an in-phase component is orthogonal to a change direction of the predetermined interference light intensity, an in-phase component in the above-described normalization difference signal z_t can be calculated by multiplying as $P^T \times a\_t$. However, in the case where the in-phase component is not orthogonal to the change in the interference light intensity, when the changes are determined as an in-phase component, changes in the intensity of interference light to be detected as an in-phase component in in-phase component removal on a latter step, for example, the intensity indicating an end point of processing may be also removed.

For example, when a phase difference is small between wavelengths in a time waveform of the interference light intensity, time changes of the intensity between a plurality of wavelengths of interference light are similar to an in-phase component and therefore might be removed as an in-phase component. In the example, to suppress the removal, an in-phase component is estimated by verifying whether the intensity of the in-phase component is a random variable following an assumed distribution. More specifically, the following processing will be performed based on the verification with respect to an assumption that the intensity of an in-phase component is a normal distribution of zero average.

First, the in-phase component estimator 205 calculates a probability in which a_k, t is an independent random variable that follows the normal distribution of zero average. This calculation is performed by calculating a T value of a t distribution by the following formula using the intensity of an in-phase component in a total f unit time of a past f–1 unit time and a current 1 unit time, a_{k,t-f+1}, . . . , a_{k, t-1}, a_k, t.

$$T\_k, t = \frac{m\_k, t}{u\_k, t / \sqrt{F}}$$

However, m_k, t is a standard mean of a_{k, t-f+1}, . . . , a{k, t-1}, a_k, t, and u_k, t is a square rood of unbiased variance a{k, t-f+1}, . . . , a_{k, t-1}, a_k, t. In the case where a_k, t is an independent random variable that follows normal distribution of zero average, T_k, t follows the t distribution represented by a probability density function by the following formula.

$$p(T\_k, t) = \frac{\Gamma((v+1)/2)}{\sqrt{v\pi}\,\Gamma(v/2)} (1 + (T\_k, t)^2 / v)^{-(v+1)/2}$$

However, "Γ" is a Gamma function, and v=F−1.

Therefore, it can be recognized that in the case where a value of p (T_k, t) is large, a_k, t indicates intensity of an in-phase component at a high probability, and in the case where a value of p (T_k, t) is low, a_k, t indicates the intensity of an in-phase component at a low probability. As a result, w_k, t is calculated by the following formula as the intensity of a new in-phase component.

$$w\_k, t = P(T\_k, t)/P(0) \times a\_k, t$$

As P(T_k, t) is a large value, in other words, P (T_k, t) indicates intensity of an in-phase component at a high probability, a value of w_k, t is increased. As P (T_k, t) is a small value, in other words, P (T_k, t) indicates intensity of an in-phase component at a low probability, a value of w_k, t is decreased. By using w_k, t, an in-phase component v_t in z_t is calculated by using the following formula.

$$v\_t = P^T \times [w\_1, t, \ldots, w\_r, t]^T$$

By calculating an in-phase component as described above, even in the case where a change in interference light intensity is not orthogonal to the in-phase component, it is suppressed that a change components other than in-phase components are removed, and while an adverse influence on other components of a signal is suppressed, in-phase components are removed. Accuracy of the detection can be improved by detecting a change in the intensity necessary to determine an etching amount and an etching end point by using an intensity signal of light from the processing chamber 102 processed as described above.

The in-phase component removing unit 206 calculates the in-phase component-removed signal x_t=z_t−v_t by subtracting the in-phase component v_t indicated by a signal estimated and sent by the in-phase component estimator 205 from the normalization difference signal z_t sent from the normalizer 202.

The integration processor 307 calculates an integral signal q_t=q {t−1}+x_t integrating the in-phase component-removed signal x_t sent from the in-phase component removing unit 206 by a time and outputs the signal as a time waveform for each wavelength. Processing by the integration processor 307 corresponds to an inverse transformation of the processing in which a difference is extracted by the a difference calculation 301.

In the example, in the processing of a time waveform signal performed by from the difference calculation unit 201 to the in-phase component estimator 205 in the in-phase component removing device 120, estimation of an in-phase component of a time waveform of the intensity of interference light detected at a past time before the certain time t during a processing period and a result of the in-phase component being removed is not affected to estimation of an in-phase component in a time waveform signal relating to the time t. Therefore, a result of removing the in-phase component being estimated from the time waveform signal relating to the time t by the in-phase component removing unit 206 is not affected by a result of the in-phase components being removed at the past time, or the influence on the result is suppressed.

Therefore, in the case where the intensity of light from the processing chamber 102 generated in a conventional technique is drastically changed, the change in the light intensity cannot be sufficiently removed by accurately following the change in the light intensity. Consequently, problems are suppressed from arising that artifacts having a skirt left for a long time is generated and that a slight light intensity change in the processing chamber 102 or from a surface of the sample 104 is buried into the artifacts and an accuracy of detecting the change is reduced. Further, a linear sum of an in-phase component base vector is deducted from a normalization difference signal, and therefore distortion generated by performing nonlinear processing in the conventional technique is suppressed, and it is suppressed that the slight light intensity change is buried into the nonlinear distortion.

Figure 3:
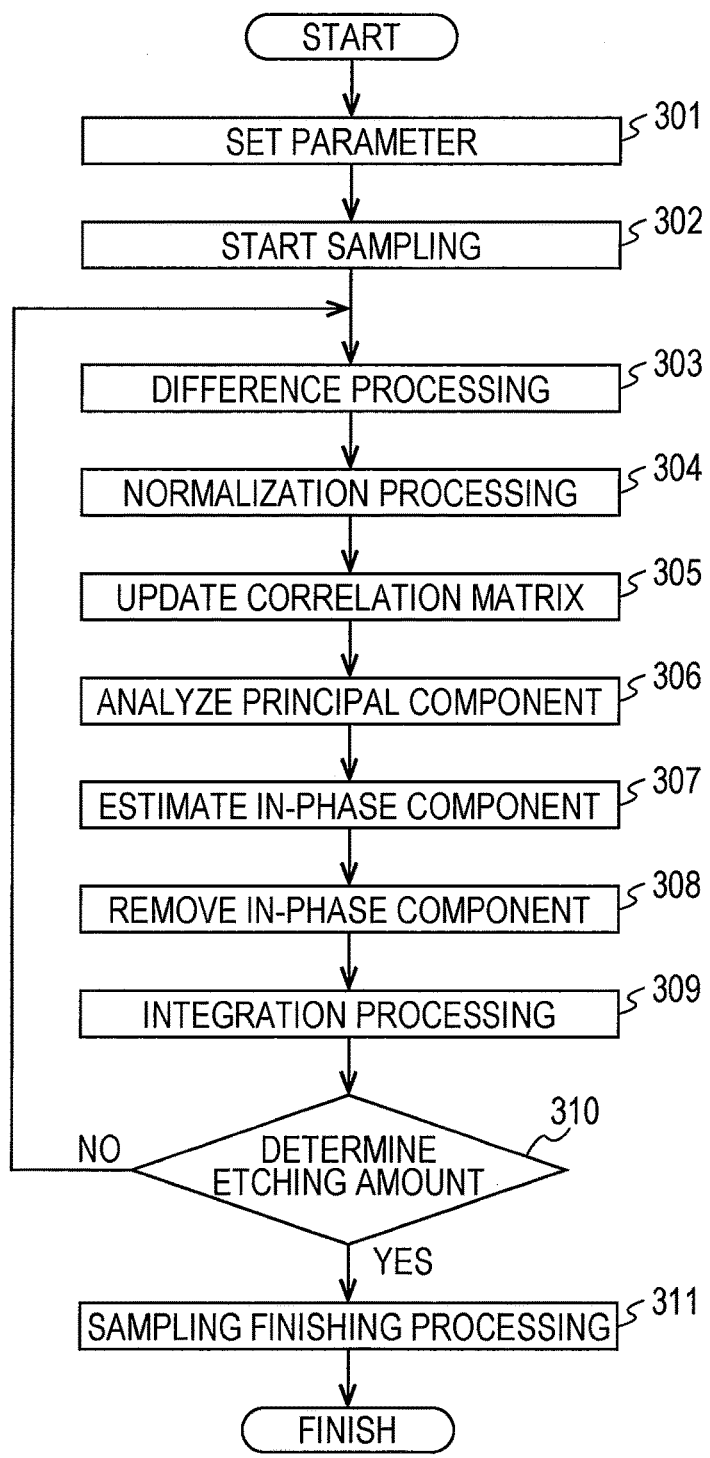
FIG. 3 is a flowchart illustrating an operation flow to determine an etching amount by the plasma processing device according to the example illustrated in FIG. 1.

FIG. 3 illustrates a flow chart of etching processing according to the example. FIG. 3 is a flowchart illustrating an operation flow to determine an etching amount by the plasma processing device according to the example illustrated in FIG. 1.

In the example, a parameter is initially set before the plasma processing device 100 performs processing on the sample 104 or before the plasma processing device 100 performs processing of data obtained when starting etching processing or during the etching processing on a film structure including a mask layer disposed in advance on a surface of the sample 104 and a film layer to be processed (step 301). In the example, the parameter is set before starting an operation.

Next, after plasma is formed in the processing chamber 102, a bias potential is formed on an upper side of a surface of the sample 104 by a high frequency power from a high frequency power source, and an etching processing on the film layer to be processed of the sample 104, detection of light from the processing chamber 102 is started (step 302). In the example, as illustrated in FIG. 2, a change in light intensity of each wavelength of spectra of predetermined multiple wavelengths obtained by receiving and diffracting light from the processing chamber 102 is detected for each time t at a sampling interval $\Delta t$. From each of light intensity signals of the multiple wavelengths detected at each interval $\Delta t$, a time difference $\Delta y\_n, t$ is calculated by a difference calculation (step 303).

Next, with respect to the signal of the obtained time difference $\Delta y\_n, t$, a time average value $\mu\_n, t$, a time standard deviation $\sigma\_n, t$, and a normalization difference signal $z\_n, t$ are detected (step 304). Further, a normalization difference signal $z\_n, t$ is used, and a correlation matrix $R\_t$ is updated for each time t (step 305).

A base vector $f\_k$ (k=1, ..., N) forming an orthonormal base corresponding to the correlation matrix and the characteristic value $\lambda\_k$ of each base vector are calculated by performing a principal component analysis to the obtained correlation matrix $R\_t$. Further, the in-phase component base vector matrix P is obtained by connecting a upper base vector of an intensity value of $c\_k$ obtained by multiplying an absolute value of an inner product of vectors b and $f\_k$ representatively indicating in-phase property by the characteristic value $\lambda\_k$ (step 306).

Next, based on the in-phase component base vector matrix P and the normalization difference signal $z\_t$, the in-phase component $v\_t$ is estimated (step 307). Further, the in-phase component $v\_t$ is subtracted and removed from the normalization difference signal $z\_t$, and an in-phase component-removed signal $x\_t$ is calculated (step 308). Then, $x\_t$ is added up by an integration processing, and an integral signal $q\_t$ is calculated as a signal of a time waveform indicating a change in the light intensity of a certain wavelength from which an in-phase component is removed (step 309).

An etching amount is determined by using a time waveform indicating a change in the intensity of light from the processing chamber 102 of one or more wavelengths obtained as described above (step 310). In the case where it is determined that a desired etching amount is achieved, detecting light from the inside of the processing chamber 102 is finished, plasma is extinguished, and also etching processing on a film layer to be processed on a surface of the sample 104 is finished (step 311). In the case where it is determined that a desired value of the etching amount is not reached, etching on the film layer is continued, and light from the inside of the processing chamber 102 is detected by the etching amount detector 110 at the following time t+$\Delta t$.

An end point of the above-described etching and an etching amount can be determined by using conventionally known means and method techniques such as detecting a change in the intensity of light emission from plasma of a wavelength regarding a reaction product from a lower film layer disposed by coming into contact with a boundary of a lower side of a film layer to be processed. Further, a conventional technique can be used to detect a residual film thickness or an etching amount from an initial film thickness by detecting a change in the intensity of interference light from boundary surfaces of a film structure including film layers disposed in advance on a surface of the sample 104 and by comparing this detection result and a pattern of a value of a residual film thickness obtained in advance and a value of an intensity or a derivative of interference light in which a wavelength is a parameter.

In the detection of light from the processing chamber 102 to detect in-phase components according to the example, a time interval $\Delta t$ for the detection is shorter than a period in which light intensity regarding the above-described end point or etching amount is changed. For example, in the case where a residual film thickness is detected by detecting a change in the intensity of interference light from a surface of the sample 104, the interval is set to be sufficiently shorter than a cycle of a change in the intensity of changing interference light which increases and decreases between a maximum and minimum intensity as etching is progressed or a period between the maximum value and the minimum value.

Figure 4:
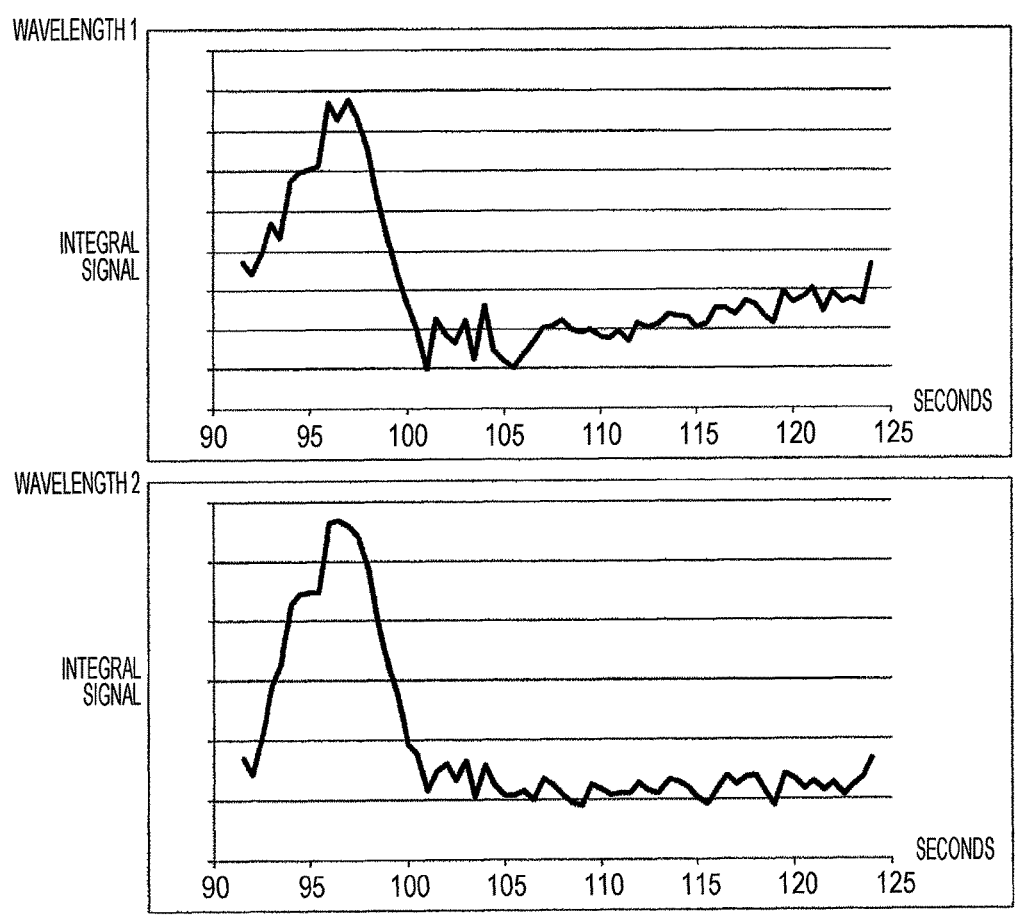
FIG. 4 is a graph illustrating a restored time waveform to indicate a change in light intensity from a processing chamber after the in-phase component detected in the example in FIG. 1 is removed.

FIG. 4 illustrates a time waveform of an integral signal according to the example. FIG. 4 is a graph illustrating a restored time waveform to indicate a change in light intensity from a processing chamber after the in-phase component detected in the example in FIG. 1 is removed. As indicated in the drawing, an in-phase component is reduced in comparison with the time waveform illustrated in FIG. 5.

The present invention is not limited to the above-described example and includes various variations. For example, the above-described example describes the present invention in detail for clarification, and every configuration described above may not be necessarily included.

Further, a configuration of an example can be partially replaced with configurations of the other examples. Furthermore, a configuration of each example can be added to configurations of the other examples. Further, a part of a configuration of each example can be added to, deleted from, and replaced with other configurations.

Further, each of the above-described configurations, functions, process units, and process means may be realized by a hardware, for example, by designing a part of or all of them by using an integrated circuit. Further, each of the configurations and the functions may be realized by a software by a processor interpreting and performing a program for realizing each function. Information such as a program, a table, and a file for realizing each function can be stored in a recording device such as a memory, a hard disc, and a solid state drive (SSD) or a recording medium such as an IC card, an SD card, and DVD.

Further, control lines and information lines which are considered to be necessary for description are indicated, and all of control lines and information lines on the product are not necessarily disclosed. In an actual device, each of many parts forming the device and an integrated unit formed by combination of the parts are connected with each other.

The invention claimed is:
1. An operation method for a plasma processing device performing etching processing by disposing a sample to be processed in a processing chamber disposed in a vacuum vessel and by using plasma generated in the processing chamber, the operation method, comprising:

detecting light intensity of a plurality of wavelengths from the inside of the processing chamber at a plurality of times during the sample processing;

detecting, by using a result of a principal component analysis of time-series data, a most highly in-phase component between the time-series data of the plurality of the wavelengths at a certain time in the plurality of times obtained from the detected light intensity; and determining an etching depth or an end point of the etching processing based on a change in the detected light intensity of at least one of the plurality of the wavelengths by using a calculated result of the most highly in-phase component being subtracted from the time-series data.

2. The operation method for the plasma processing device according to claim 1, wherein an interval between the plurality of times is smaller than a time required to change between a maximum value and a minimum value of the light intensity.

3. The operation method for the plasma processing device according to claim 1, wherein the time-series data of the light intensity of the plurality of the wavelength is obtained from an output of a light detector.

4. The operation method for the plasma processing device according to claim 1, wherein the most highly in-phase component is generated by synchronizing the time-series data of the light intensity of the plurality of the wavelengths obtained from an output of a light detector.

5. The operation method for the plasma processing device according to claim 1, wherein the most highly in-phase component is detected based on a probability in which the light intensity of the most highly in-phase component is a random variable that follows a predetermined distribution.

* * * * *